United States Patent
Ren et al.

(10) Patent No.: US 10,168,329 B2
(45) Date of Patent: Jan. 1, 2019

(54) N-ACETYL-D-GLUCOSAMINE FOR ENHANCED SPECIFICITY OF STREP A IMMUNOASSAY

(75) Inventors: Peter Yan-Guo Ren, San Diego, CA (US); Jason McClure, San Diego, CA (US); Kevin S. Richardson, San Diego, CA (US)

(73) Assignee: Quidel Corporation, San Diego, CA (US)

( * ) Notice: Subject to any disclaimer, the term of this patent is extended or adjusted under 35 U.S.C. 154(b) by 205 days.

(21) Appl. No.: 13/563,542

(22) Filed: Jul. 31, 2012

(65) Prior Publication Data

US 2013/0196337 A1    Aug. 1, 2013

Related U.S. Application Data

(60) Provisional application No. 61/514,790, filed on Aug. 3, 2011.

(51) Int. Cl.
G01N 33/558    (2006.01)
G01N 33/569    (2006.01)
G01N 33/543    (2006.01)

(52) U.S. Cl.
CPC . *G01N 33/56944* (2013.01); *G01N 33/54393* (2013.01); *G01N 33/558* (2013.01)

(58) Field of Classification Search
None
See application file for complete search history.

(56) References Cited

U.S. PATENT DOCUMENTS

| | | | |
|---|---|---|---|
| 5,415,994 A | 5/1995 | Imrich et al. | |
| 5,763,262 A | 6/1998 | Wong et al. | |
| 5,770,460 A | 6/1998 | Pawlak et al. | |
| 7,601,546 B2 * | 10/2009 | Bayliff et al. | 436/514 |

FOREIGN PATENT DOCUMENTS

| | | |
|---|---|---|
| EP | 2031392 A1 | 3/2009 |
| JP | H02-177899 A | 7/1990 |
| JP | H03-152466 A | 6/1991 |
| JP | H06-018524 A | 1/1994 |
| JP | H07-036018 B | 4/1995 |
| JP | H08-240592 A | 9/1996 |
| JP | 2601498 B2 | 4/1997 |
| JP | 2001-289852 A | 10/2001 |
| WO | WO 1984/004169 A1 | 10/1984 |
| WO | WO 1988/002781 A1 | 10/1987 |
| WO | WO 1990/010232 A1 | 9/1990 |
| WO | WO 1995/004280 A1 | 2/1995 |
| WO | WO 1999/005524 A1 | 2/1999 |
| WO | WO 2008/073895 A2 | 6/2008 |

OTHER PUBLICATIONS

Millipore et al. (Millipore "Rapid lateral flow test strips" 2008 Lit. No. TB500EN00 Rev. B May 2008).*
Poulsen et al. ( "Purification of Anti *Streptococcus* Group A Antibodies by affinity Chromatography and Isoelectric Focusing" Carlsberg Res. Commun. vol. 42, p. 397-405, 1977).*
Blank et al., "Overlapping humoral autoimmunity links rheumatic fever and the antiphospholipid syndrome", Rheumatology, vol. 45, pp. 833-841 (2006).
Cunningham, "Autoimmunity and molecular mimicry in the pathogenesis of post-*Streptococcal* heart disease", Front Biosci., vol. 1, pp. s533-s543 (2003).
Poulsen and Johansen, "Purification of anti *Streptococcus* group A antibodies by affinity chromatography and isoelectric focusing", Carlsberg Res. Commun., vol. 42. pp. 397-405 (1977).
Ohkuni, "Culturette brand ten-minute group A Strep ID", J. Japanese Assoc. Inf. Dis., vol. 59, No. 12, pp. 1204-1209 (1985) *English Abstract*.

* cited by examiner

*Primary Examiner* — Tracy Vivlemore
*Assistant Examiner* — Daniela E Fuentes
(74) *Attorney, Agent, or Firm* — McDermott Will & Emery LLP

(57) ABSTRACT

Methods, compositions and kits for detecting Group A *streptococcus* in a biological sample are described. More particularly, the present disclosure provides an immunoassay in which the specificity of detection of Group A *streptococcus* is enhanced by addition of N-acetyl-D-glucosamine. These methods, compositions and kits are useful in convenient, reliable and early diagnosis of streptococcal infection in a human subject.

8 Claims, 9 Drawing Sheets

Figure 1:
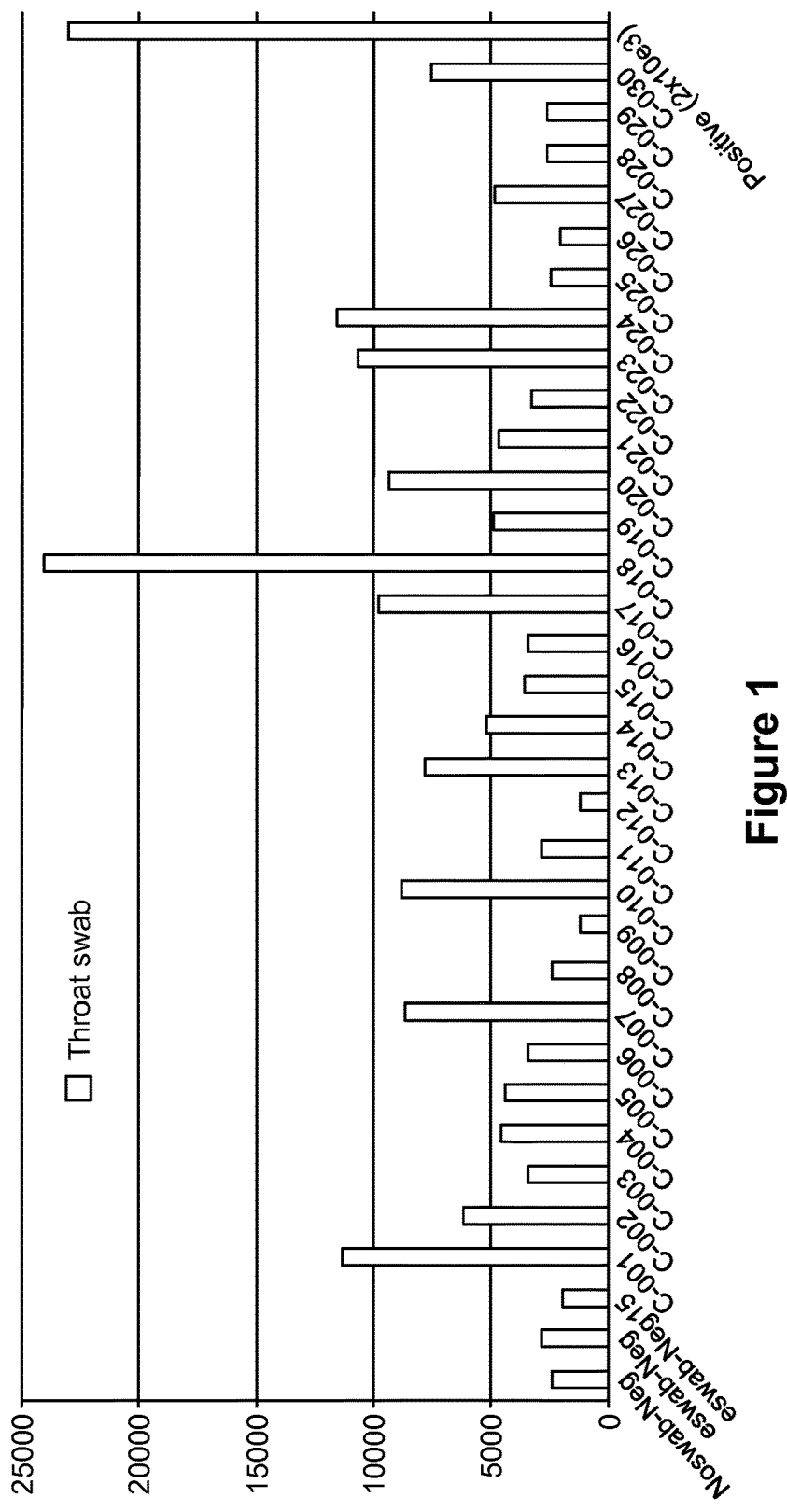

Sensitivity and Specificity Against Cell Culture and Resolved by QV Strep A Dipstick

|  |  | + | - |  |  |
|---|---|---|---|---|---|
| Strep A FL | + | True Positive 32 | False Positive 5 | All with Positive Test 37 | Positive Predictive Value = 89.19% |
|  | - | False Negative 2 | True Negative 95 | All with Negative Test 97 | Predictive Negative Value = 98.97% |
|  |  | All with Disease 34 | All without Disease 100 | Everyone = 134 | |
|  |  | Sensitivity = 94.1% | Specificity = 95.0% | Pre-Test Probability = % Test Population with Disease 25% | |
| 95% CI's |  | 79.9 - 99.4% | 88.7 - 98.2% | | |

Figure 9

N-ACETYL-D-GLUCOSAMINE FOR ENHANCED SPECIFICITY OF STREP A IMMUNOASSAY

CROSS-REFERENCE TO RELATED APPLICATIONS

This application claims the benefit of U.S. Application No. 61/514,790, filed Aug. 3, 2011, which is incorporated by reference herein.

TECHNICAL FIELD

The present disclosure generally relates to the field of diagnostics, and, in particular, to devices, methods and kits for detecting analytes in biological samples. More particularly, the present disclosure provides an immunoassay in which the specificity of detection of Group A *streptococcus* is enhanced by addition of N-acetyl-D-glucosamine.

BACKGROUND

*Streptococcus pyogenes* (Group A *streptococcus*) is a Gram-positive, nonmotile, non-sporeforming bacterium that occurs in chains or in pairs of cells, where individual cells are round-to-ovoid cocci, 0.6-1.0 micrometer in diameter. The cell surface structure of Group A streptococci is composed of repeating units of N-acetylglucosamine and N-acetylmuramic acid, the standard peptidoglycan. Historically, the definitive identification of streptococci has rested on the serologic reactivity of "cell wall" polysaccharide antigens as originally described by Rebecca Lancefield. Eighteen group-specific antigens (Lancefield groups) were established. The Group A capsular polysaccharide (also called "C substance" or "group carbohydrate antigen") is a polymer of N-acetylglucosamine and rhamnose. Some group antigens are shared by more than one species. (K. Todar, Online Textbook of Bacteriology; See textbookofbacteriology.net).

*S. pyogenes* is one of the most frequent pathogens of humans. Approximately 5-15% of normal individuals harbor the bacterium, usually in the respiratory tract, yet remain asymptomatic. As normal flora, *S. pyogenes* can infect when defenses are compromised or when the organisms are able to penetrate the constitutive defenses. When the bacteria are introduced or transmitted to vulnerable tissues, a variety of types of suppurative infections can occur.

Acute diseases associated with *S. pyogenes* occur mainly in respiratory tract, bloodstream or skin. Streptococcal disease is most often a respiratory infection (pharyngitis or tonsillitis) or a skin infection (pyoderma). Acute *S. pyogenes* infections may present as pharyngitis (strep throat), scarlet fever (rash), impetigo (infection of the superficial layers of the skin) or cellulitis (infection of the deep layers of the skin). Invasive, toxigenic infections can result in necrotizing fasciitis, joint or bone infections, myositis, meningitis, endocarditis and streptococcal toxic shock syndrome. Patients may also develop immune-mediated post-streptococcal sequelae, such as acute rheumatic fever and acute glomerulonephritis, following acute infections caused by *S. pyogenes*, which occur in 1-3% of untreated infections. These conditions and their pathology are not attributable to dissemination of bacteria, but to aberrant immunological reactions to Group A streptococcal antigens.

Because penicillin is effective in treatment of Group A streptococcal disease, the majority of infections amount to no more than pharyngitis accompanied by a rash. However, due to the occasional cases of rapidly progressive disease and because of the small risk of serious sequelae in untreated infections, *S. pyogenes* remains a major health concern, and effort is being directed toward clarifying the risk and mechanisms of these sequelae and identifying rheumatogenic and nephritogenic strains of streptococci.

The cell surface of *S. pyogenes* accounts for many of the bacterium's determinants of virulence, especially those concerned with colonization and evasion of phagocytosis and the host immune responses. The surface of the bacterium is incredibly complex and chemically-diverse. Antigenic components include capsular polysaccharide (C-substance), cell wall peptidoglycan and lipoteichoic acid (LTA), and a variety of surface proteins, including M protein, fimbrial proteins, fibronectin-binding proteins, (e.g. Protein F) and cell-bound streptokinase.

The cytoplasmic membrane of *S. pyogenes* contains some antigens similar to those of human cardiac, skeletal, and smooth muscle, heart valve fibroblasts, and neuronal tissues. Molecular mimicry between pathogen and host has been proposed as a mechanism for the development of autoimmune diseases. Because microorganisms contain proteins similar to host proteins, the host's immune response may be suppressed or tolerant to infection. Conversely, stimulation of the host's B and T cells by a molecular mimic can cause the host's immune system to begin responding to self proteins as if they are foreign.

As in other autoimmune diseases, both environmental and genetic factors are involved in the development of rheumatic carditis and inflammatory heart disease, and molecular mimicry between the group A *streptococcus* and heart tissues appears to play a role. The study of B and T cell responses against group A streptococcal antigens has yielded some information about several steps in the pathogenesis of rheumatic carditis following group A streptococcal infection. An early step involves the development of crossreactive autoantibodies against the group A streptococcal carbohydrate antigen N-acetyl-glucosamine and cardiac myosin. These antibodies then react with valvular endothelium, which becomes inflamed with expression of vascular cell adhesion molecule-1 (VCAM-1). T cells, CD4+ and CD8+, then infiltrate through the endothelium/endocardium into the valve (an avascular structure). Aschoff bodies or granulomatous lesions may form containing macrophages and T cells underneath the endocardium. The T cells are responsive to streptococcal M protein antigen sequences. The valve becomes scarred with eventual neovascularization and progressive, chronic disease in the valve. In the host, the mimicking antigens cardiac myosin and laminin have been involved in the myocardium and valve, respectively. (Cunningham, Front. Biosci., 2003, 8:s533-43).

Rheumatic fever (RF) and the antiphospholipid syndrome (APS) are autoimmune diseases sharing similar cardiac and neurological pathologies. There appears to be a considerable overlap of humoral immunity in RF and APS, supporting a hypothesis that common pathogenic mechanisms underlie the development of cardiac valve lesions and Central Nervous System abnormalities in both diseases. The pathogenic molecules engaged in these autoimmune conditions, M protein, N-acetyl-beta-D-glucosamine (also called "NAG" or "GlcNAc") and beta2 glycoprotein-I (beta2GPI), were found to share some epitopes. The immunoglobulin G sera from APS patients contained a considerable anti-streptococcal M protein as well as anti-GlcNAc activity. Furthermore, beta2GPI inhibited anti-GlcNAc activity from APS patients with chorea. (Blank, et al., 2006, Rheumatology (Oxford). 45(7):833-41).

Detection of microbial pathogens in biological samples is of particular value in clinical medicine, as treatment may vary considerably depending upon the causative organism. Thus, the accurate and rapid identification of pathogens in biological samples of patients suspected of having an infectious disease can be critical to provide prompt and appropriate treatment to patients. Rapid identification of disease-causing organisms in biological samples is important even for non-life threatening infections.

Rapid methods of diagnosing microbial infections have been developed to provide timely results for guiding clinical therapy. Some of the most effective of these rapid methods have been immunologically based. Monoclonal and polyclonal antibodies to microbe-specific antigens have been developed and used in immunoassays to identify specific microbes in biological samples. For example, immunoassays for the identification of group A streptococcal antigens in human samples are useful for the early detection of *S. pyogenes* infection, so that proper antibiotic treatment may be started.

Group A *Streptococcus* in pharyngeal exudates can be identified by polyclonal antibodies to antigens specific for Group A *streptococcus*. One such test is described in U.S. Pat. No. 5,770,460, providing a one-step lateral flow assay for Group A *streptococcus*-specific antigens. However, tests relying on pharyngeal swabs are often complicated by a high false positive rate. Although instructions for use of pharyngeal swab tests specifically direct the user to avoid contacting the tongue, cheek and/or teeth with the swab, inadvertent contact often occurs, nonetheless. Epithelial cells originating from the tongue, cheek and/or teeth may contain molecular mimics of one or more components of the *S. pyogenes* cell wall, and the polyclonal antibody specific for Group A *streptococcus* may bind and "recognize" epitopes on the epithelial cells in a test subject not infected by or carrying Group A strep, resulting in a false positive result. A highly specific and facile immunoassay with a reduced rate of false positives is needed to provide accurate detection of Group A *streptococcus* infection. Quite surprisingly, the present disclosure fulfills these and other related needs.

BRIEF SUMMARY

The present disclosure provides devices, methods and improved diagnostic kits for detecting Group A *streptococcus* (also referred to herein as "Strep A") in biological samples. More particularly, the present disclosure provides an improved immunoassay in which Group A streptococcal infection is detected with a reduced rate of false-positive results via addition of N-acetyl-D-glucosamine to the assay.

In one aspect, a device for detecting the presence of Group A *streptococcus* in a sample is provided. The device comprises a matrix having (i) a sample receiving zone for receiving a sample containing or suspected of containing a Group A *streptococcus*-specific antigen, (ii) a labeling zone containing an antibody for specifically labeling the antigen as it passes therethrough and (iii) a capture zone having means for specifically binding the labeled antigen thereon, wherein the sample receiving zone, the labeling zone and the capture zone are arranged on the matrix in a liquid flow path, and wherein at least one of the sample receiving zone and the labeling zone comprise N-acetyl-D-glucosamine (NAG).

In one embodiment, the antibody is a polyclonal antibody.

In another embodiment, the antibody is fluorescently labeled.

In still another embodiment, the means for specifically binding the labeled antigen is a capture antibody. In one embodiment, the capture antibody is a polyclonal antibody.

In another aspect, a kit is provided. The kit comprises a device comprising a matrix having (i) a sample receiving zone for receiving a sample containing or suspected of containing a Group A *streptococcus*-specific antigen, (ii) a labeling zone containing an antibody for specifically labeling the antigen as it passes therethrough and (iii) a capture zone having means for specifically binding the labeled antigen thereon, wherein the sample receiving zone, the labeling zone and the capture zone are arranged on the matrix in a liquid flow path; and a container comprising an extraction reagent. At least one of the extraction reagent, the sample receiving zone and the labeling zone comprise N-acetyl-D-glucosamine (NAG).

In one embodiment, NAG is deposited on the sample receiving zone.

In another aspect, a method for detecting the presence or absence of Group A *streptococcus* in a biological sample is provided. The method comprises providing a device or a kit as described herein placing a biological sample on the device; and determining the presence or absence of Group A *streptococcus*, for example by visually reading (with the unaided eye, with an instrument, or with the eye assisted by an instrument) the result on the test line of the device.

In one embodiment, the method further comprises providing an instrument for collecting the biological sample; and collecting a biological sample on the instrument.

In still another embodiment, the method further comprises providing instructions for use, wherein the instructions do not caution to not touch the tongue, sides or top of mouth with the instrument when collecting the sample.

In another aspect, a kit is provided. The kit comprises a device according to any of the embodiments described herein, a container comprising an extraction reagent; and an instrument for collecting a biological sample; and instructions for use.

In one embodiment, the instrument is a swab.

In another embodiment, the instructions do not caution to not touch the tongue, sides or top of mouth with the instrument when collecting the sample.

In still another aspect, a method to reduce the false positive rate of a lateral flow assay in the detection of Group A *streptococcus* in a sample, wherein, in the lateral flow assay, N-acetyl-D-glucosamine (NAG)-binding components of a polyclonal antibody label used in the assay are preferentially bound is provided. The method comprise treating a bibulous matrix with an amount of N-acetyl-D-glucosamine (NAG) effective as a blocking agent to enhance the specific binding of the polyclonal antibody to Group A *streptococcus* antigen and reduce the false positive rate of the assay.

In one embodiment, a device for detecting the presence of Group A *streptococcus* in a sample is provided. The device comprises a receiving chamber for receiving a sample suspected of comprising Group A *streptococcus*-specific antigen, the chamber dimensioned to receive a liquid extraction reagent and N-acetyl-D-glucosamine (NAG) that combine with the sample to form a treated sample; and a matrix having a sample receiving zone for receiving the treated sample, a labeling zone having a polyclonal antibody for specifically labeling the antigen as it passes therethrough and a capture zone having means for specifically binding the labeled antigen thereon, wherein the sample receiving zone, the labeling zone and the capture zone are arranged on the matrix in a liquid flow path.

In another embodiment, a method for detecting the presence of Group A *streptococcus* in a sample is provided. The method comprises providing a matrix having (i) a sample receiving zone for receiving a sample containing or suspected of containing a Group A *streptococcus*-specific antigen, (ii) a labeling zone containing an antibody for specifically labeling the antigen as it passes therethrough and (iii) a capture zone having means for specifically binding the labeled antigen thereon, wherein the sample receiving zone, the labeling zone and the capture zone are arranged on the matrix in a liquid flow path, and contacting the sample receiving zone with the sample, wherein said sample is treated with a liquid reagent comprising N-acetyl-D-glucosamine (NAG) prior to contacting; and detecting the presence or absence of the antigen in the capture zone.

In another embodiment, a device for detecting the presence of Group A *streptococcus* in a sample is provided. The device comprises a receiving chamber for receiving a sample suspected of comprising Group A *streptococcus*-specific antigen, the chamber dimensioned to receive a liquid extraction reagent that contacts the sample to provide a treated sample; and a matrix having a sample receiving zone for receiving the treated sample, a labeling zone containing N-acetyl-D-glucosamine (NAG) and a polyclonal antibody for specifically labeling the antigen as it passes therethrough and a capture zone having means for specifically binding the labeled antigen thereon, wherein the sample receiving zone, the labeling zone and the capture zone are arranged on the matrix in a liquid flow path.

In yet another embodiment, a device for detecting the presence of Group A *streptococcus* in a sample is provided. The device comprises a receiving chamber for receiving a sample suspected of comprising Group A *streptococcus*-specific antigen, the chamber dimensioned to receive a liquid extraction reagent that contacts the sample to provide a treated sample; and a matrix having a sample receiving zone for receiving the treated sample, a labeling zone containing a polyclonal antibody for specifically labeling the antigen as it passes therethrough and a capture zone containing N-acetyl-D-glucosamine (NAG) and a means for specifically binding the labeled antigen thereon, wherein the sample receiving zone, the labeling zone and the capture zone are arranged on the matrix in a liquid flow path.

In still another embodiment, a method to reduce the false positive rate of a lateral flow assay in the detection of Group A *streptococcus* in a sample is provided, where in the lateral flow assay, N-acetyl-D-glucosamine (NAG)-binding components of a polyclonal antibody label used in the assay are preferentially bound. The method comprises adding to an extraction reagent, or to a localized region of the immunoassay test strip an amount of N-acetyl-D-glucosamine (NAG) effective as a blocking agent to enhance the specific binding of the polyclonal antibody to Group A *streptococcus* antigen and reduce the false positive rate of the assay.

In another embodiment, an improvement in an immunoassay device for detecting Group A *streptococcus* having a housing with at least one opening therethrough for introduction of a liquid sample into the housing, an extraction reagent, a sample receiving zone of porous material in said housing to be contacted by said liquid sample, and a polyclonal antibody labeling agent in a labeling zone is provided. The improvement comprises N-acetyl-D-glucosamine (NAG) added to the sample receiving zone in an amount effective as a blocking agent to enhance the specific binding of the polyclonal antibody to Group A *streptococcus* antigen and reduce the false positive rate of the assay.

In still another embodiment, an improvement in an immunoassay device for detecting Group A *streptococcus* having a housing with at least one opening therethrough for introduction of a liquid sample into the housing, an extraction reagent, a sample receiving zone of porous material in said housing to be contacted by said liquid sample, and a polyclonal antibody labeling agent in a labeling zone is provided. The improvement comprises N-acetyl-D-glucosamine (NAG) added to the labeling zone in an amount effective as a blocking agent to enhance the specific binding of the polyclonal antibody to Group A *streptococcus* antigen and reduce the false positive rate of the assay.

In yet another embodiment, an improvement in an immunoassay device for detecting Group A *streptococcus* having a housing with at least one opening therethrough for introduction of a liquid sample into the housing, an extraction reagent, a sample receiving zone of porous material in said housing to be contacted by said liquid sample, and a polyclonal antibody labeling agent in a labeling zone is provided. The improvement comprises N-acetyl-D-glucosamine (NAG) added to the extraction reagent in an amount effective as a blocking agent to enhance the specific binding of the polyclonal antibody to Group A *streptococcus* antigen and reduce the false positive rate of the assay.

The following aspects and embodiments thereof described and illustrated below are meant to be exemplary and illustrative, not limiting in scope.

BRIEF DESCRIPTION OF THE FIGURES

FIG. 1 is a bar graph showing the absolute count of Strep A antigen in throat swabs taken from healthy individuals (C-001 to C-030), in negative and positive control samples, each tested using a lateral flow diagnostic immunoassay for Strep A;

FIG. 2 is a bar graph showing the absolute value of the signal at the test line in Strep A immunoassay devices for samples collected from the saliva (whole and fractions after centrifugation), cheek, tongue, nose, ear and skin of a human, and from the laboratory bench top surface;

FIG. 3 is a bar graph showing the absolute value of the signal at the test line of a Strep A immunoassay device for saliva samples from healthy individuals (C-001-C-0030) where a known quantity of anti-group A strep antibody was added to the extraction reagent when preparing the samples for deposition on the immunoassay;

FIG. 4 is a bar graph showing the relative signal observed at the test line of an immunoassay device for detection of Strep A for tongue swab samples prepared for testing on the device by including the indicated chemical compound in the extraction reagent;

FIG. 5 illustrates an exemplary immunoassay device;

FIG. 6 is a graph of relative signal at the test line of an immunoassay device for Strep A as a function of concentration of NAG present in the extraction reagent for tongue swab samples (diamonds) and for a Strep A quality control standard of $2\times10^3$ organisms/test (squares);

FIG. 7 is a bar graph showing the data presented in FIG. 1 and the sample samples tested again on an immunoassay Strep A detection strip with 0.5 mg/mL NAG added to the extraction reagent (right hand bar in each of the data sets for each of the indicated patients);

FIG. 8 is a bar graph showing the absolute signal at the test line of a Strep A immunoassay device comprising NAG in the sample pad of the device by depositing, and allowing to dry, a solution to the sample pad of NAG at concentrations of 0.4 mg/mL, 0.6 mg/mL, 0.8 mg/mL and 1 mg/mL and testing for signal upon application of saline (negative control, left bar in each data set), a quality control standard of $2 \times 10^3$ organisms/test (middle bar in each data set) and a tongue swab (right bar in each data set); and FIG. 9 is a table showing the calculation of the sensitivity, specificity, positive and negative predictive values of an immunoassay for Group A *streptococcus* improved with the addition of NAG, in accord with the invention herein.

These and other embodiments are further described in the detailed description that follows.

DETAILED DESCRIPTION

I. Definitions

Before the present methods and compositions are described, it is to be understood that this disclosure is not limited to particular embodiments described, as such may, of course, vary. Several embodiments of the present disclosure are described in detail hereinafter. These embodiments may take many different forms and should not be construed as limited to those embodiments explicitly set forth herein. Rather, these embodiments are provided so that this disclosure will be thorough and complete, and will fully convey the scope of the present disclosure to those skilled in the art. It is also to be understood that the terminology used herein is for the purpose of describing particular embodiments only, and is not intended to be limiting, since the scope of the invention will be limited only by the appended claims.

All patents, applications, published applications and other publications referred to herein are incorporated by reference in their entirety.

As used herein, the following terms are intended to have the following meanings:

As used herein, the singular forms "a," "an," and "the" include plural referents unless the context clearly dictates otherwise. Thus, for example, reference to "a protein" includes a plurality of such proteins and reference to "the formulation" includes reference to one or more formulations and equivalents thereof known to those skilled in the art, and so forth.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed by this disclosure. The upper and lower limits of these smaller ranges may independently be included or excluded in the range, and each range where either, neither or both limits are included in the smaller ranges is also encompassed by this disclosure, subject to any specifically excluded limit in the stated range. Where the stated range includes one or both of the limits, ranges excluding either or both of those included limits are also within the scope of this disclosure.

"Protein," "polypeptide," "oligopeptide," and "peptide" are used interchangeably to denote a polymer of at least two amino acids covalently linked by an amide bond, regardless of length or post-translational modification (e.g., glycosylation, phosphorylation, lipidation, myristilation, ubiquitination, etc.). Included within this definition are D- and L-amino acids, and mixtures of D- and L-amino acids.

N-Acetylglucosamine (also called "N-acetyl-D-glucosamine," "NAG" or "GlcNAc") is a monosaccharide derivative of glucose having a molecular formula of $C_8H_{15}NO_6$, a molar mass of 221.21 g/mol. It is part of a biopolymer in bacterial cell walls, and, in particular, the cell surface structure of *Streptococcus pyogenes* (Group A *streptococcus*) comprises alternating units of NAG and N-acetylmuramic acid (MurNAc), cross-linked with oligopeptides at the lactic acid residue of MurNAc. This layered structure is called peptidoglycan. NAG is the monomeric unit of the polymer chitin, which forms the exoskeletons of insects and crustaceans. NAG polymerized with glucuronic acid forms hyaluronan, a component of connective, epithelial and neural tissues of higher organisms.

The term "sequence identity" means nucleic acid or amino acid sequence identity in two or more aligned sequences, aligned using a sequence alignment program.

Exemplary computer programs which can be used to determine identity between two sequences include, but are not limited to, the suite of BLAST programs, e.g., BLASTN, BLASTX, and TBLASTX, BLASTP and TBLASTN, publicly available on the Internet at (ncbi.nlm.gov/BLAST/). See, also, Altschul, S. F. et al., 1990 and Altschul, S. F. et al., 1997.

"Percentage of sequence identity" and "percentage homology" are used interchangeably herein to refer to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage may be calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Alternatively, the percentage may be calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Those of skill in the art appreciate that there are many established algorithms available to align two sequences. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the GCG Wisconsin Software Package), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)). Examples of algorithms that are suitable for determining percent sequence identity and sequence similarity are the BLAST and BLAST 2.0 algorithms, which are described in Altschul et al. (1990) J. Mol. Biol. 215: 403-410 and Altschul et al. (1977) Nucleic Acids Res. 3389-3402, respectively. Software for performing BLAST analyses is publicly available through the National Center for Biotechnology Information website. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Natl. Acad. Sci. USA 89:10915 (1989)).

While all of the above mentioned algorithms and programs are suitable for a determination of sequence alignment and % sequence identity, for purposes of the disclosure herein, determination of % sequence identity will typically be performed using the BESTFIT or GAP programs in the GCG Wisconsin Software package (Accelrys, Madison Wis.), using default parameters provided.

The phrase "% sequence identity" refers to the level of nucleic acid or amino acid sequence identity between two or more aligned sequences, when aligned using a sequence alignment program. For example, 70% homology means the same thing as 70% sequence identity determined by a defined algorithm, and accordingly a homologue of a given sequence has greater than 70% sequence identity over a length of the given sequence. Exemplary levels of sequence identity include, but are not limited to 70%, 75% 80%, 85%, 90% or 95%, 96%, 97%, 98% or 99% sequence identity to a given sequence, e.g., the nucleic acid or amino acid sequence of a protein, as described herein.

"Associated" refers to coincidence with the development or manifestation of a disease, condition or phenotype. Association may be due to, but is not limited to, genes responsible for housekeeping functions whose alteration can provide the foundation for a variety of diseases and conditions, those that are part of a pathway that is involved in a specific disease, condition or phenotype and those that indirectly contribute to the manifestation of a disease, condition or phenotype.

As pertains to the present disclosure, a biological fluid can be a solid, or semi-solid sample, including feces, biopsy specimens, skin, nails, and hair, or a liquid sample, such as urine, saliva, sputum, mucous, blood, blood components such as plasma or serum, amniotic fluid, semen, vaginal secretions, tears, spinal fluid, washings, and other bodily fluids. Included among the sample are swab specimens from, e.g., the cervix, urethra, nostril, and throat. Any of such samples may be from a living, dead, or dying animal or a plant. Animals include mammals, such as humans.

"Antibody" refers to a polypeptide substantially encoded by an immunoglobulin gene or immunoglobulin genes, or fragments thereof. The recognized immunoglobulin genes include the kappa, lambda, alpha, gamma, delta, epsilon, and mu constant regions, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively. Typically, an antibody is an immunoglobulin having an area on its surface or in a cavity that specifically binds to and is thereby defined as complementary with a particular spatial and polar organization of another molecule. The antibody can be polyclonal or monoclonal. Antibodies may include a complete immunoglobulin or fragments thereof. Fragments thereof may include Fab, Fv and F(ab')2, Fab', and the like. Antibodies may also include chimeric antibodies or fragment thereof made by recombinant methods.

"Antibody" includes whole antibodies, including those of the IgG, IgM and IgA isotypes, and any antigen binding fragment (i.e., "antigen-binding portion") or single chain thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as VH) and a heavy chain constant region. The IgG heavy chain constant region is comprised of four domains, CH1, hinge, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

"Isolated antibody," as used herein, is intended to refer to an antibody which is substantially free of other antibodies having different antigenic specificities (e.g., an isolated antibody that specifically binds to the protein of interest is substantially free of antibodies that specifically bind antigens other than the protein of interest). An isolated antibody that specifically binds to an epitope, isoform or variant of the protein of interest may, however, have cross-reactivity to other related antigens, e.g., from other species (e.g., species homologs). Moreover, an isolated antibody may be substantially free of other cellular material and/or chemicals. In some embodiments, a combination of "isolated" monoclonal antibodies having different specificities are combined in a well-defined composition.

"Specific binding" refers to antibody binding to a predetermined antigen. Typically, the antibody binds with a dissociation constant (KD) of $10^{-7}$ M or less, and binds to the predetermined antigen with a KD that is at least two-fold less than its KD for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen".

"Immunological binding," as used herein, generally refers to the non-covalent interactions of the type that occurs between an antibody, or fragment thereof, and the type 1 interferon or receptor for which the antibody is specific. The strength, or affinity, of immunological binding interactions can be expressed in terms of the dissociation constant (Kd) of the interaction, wherein a smaller Kd represents a greater affinity. Immunological binding properties of selected antibodies can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" (Kon) and the "off rate constant" (Koff) can be determined by calculation of the concentrations and the actual rates of association and dissociation. The ratio of Koff/Kon enables cancellation of all parameters not related to affinity, and is thus equal to the dissociation constant Kd. See, generally, Davies et al., *Annual Rev. Biochem.* 59:439-473 (1990).

"High affinity" for an IgG antibody refers to an antibody having a KD of $10^{-8}$ M or less, more preferably $10^{-9}$ M or less and even more preferably $10^{-10}$ M or less. However, "high affinity" binding can vary for other antibody isotypes. For example, "high affinity" binding for an IgM isotype refers to an antibody having a KD of $10^{-7}$ M or less, more preferably $10^{-8}$ M or less.

Monoclonal antibodies to a compound may be prepared using any technique which provides for the production of antibody molecules by continuous cell lines in culture. These include, but are not limited to, the hybridoma technique originally described by Kohler & Milstein, 1975, Nature 256:495-497 and/or Kaprowski, U.S. Pat. No. 4,376,110; the human B-cell hybridoma technique described by Kosbor et al., 1983, Immunology Today 4:72 and/or Cote et al., 1983, Proc. Natl. Acad. Sci. USA 80:2026-2030; and the EBV-hybridoma technique described by Cole et al., 1985, Monoclonal Antibodies and Cancer Therapy, Alan R. Liss, Inc., pp. 77-96. In addition, techniques developed for the production of "chimeric antibodies" (Morrison et al., 1984, Proc. Natl. Acad. Sci. USA 81:6851-6855; Neuberger et al., 1984, Nature 312:604-608; Takeda et al., 1985, Nature 314:452-454; Boss, U.S. Pat. No. 4,816,397; Cabilly, U.S. Pat. No. 4,816,567) by splicing the genes from a mouse antibody molecule of appropriate antigen specificity together with genes from a human antibody molecule of appropriate biological activity can be used. Or "humanized" antibodies can be prepared (see, e.g., Queen, U.S. Pat. No. 5,585,089). Alternatively, techniques described for the production of single chain antibodies (see, e.g., U.S. Pat. No. 4,946,778) can be adapted to produce compound-specific single chain antibodies.

Antibody fragments which contain deletions of specific binding sites may be generated by known techniques. For example, such fragments include but are not limited to F(ab')2 fragments, which can be produced by pepsin digestion of the antibody molecule and Fab fragments, which can be generated by reducing the disulfide bridges of the F(ab')2 fragments. Alternatively, Fab expression libraries may be constructed (Huse et al., 1989, Science 246:1275-1281) to allow rapid and easy identification of monoclonal Fab fragments with the desired specificity for the peptide of interest.

The antibody or antibody fragment specific for the desired peptide can be attached, for example, to agarose, and the antibody-agarose complex is used in immunochromatography to purify peptides. See, Scopes, 1984, Protein Purification: Principles and Practice, Springer-Verlag New York, Inc., N.Y., Livingstone, 1974, Methods In Enzymology: Immunoaffinity Chromatography of Proteins 34:723-731.

"Detect" and "detection" have their standard meaning, and are intended to encompass detection, measurement and/or characterization of a selected protein or protein activity. For example, enzyme activity may be "detected" in the course of detecting, screening for, or characterizing inhibitors, activators, and modulators of the protein.

The term "reference level" refers to a detected level of a positive or negative control. For example, a reference level of a positive control can be a known amount of Group A *streptococcus*-specific antigen, obtained from a sample or culture of a known Group A *streptococcus* bacterium, a subject known to be infected with Group A *streptococcus*, or can refer to a numerical value derived from known sources of Group A *streptococcus*-specific antigen.

"Label" refers to any moiety that, when attached to a moiety described herein, e.g., a peptide, protein or antibody, renders such a moiety detectable using known detection methods, e.g., spectroscopic, photochemical, electrochemiluminescent, and electrophoretic methods. Various labels suitable for use in the present disclosure include labels which produce a signal through either chemical or physical means, wherein the signal is detectable by visual or instrumental means. Exemplary labels include, but are not limited to, fluorophores and radioisotopes. Such labels allow direct detection of labeled compounds by a suitable detector, e.g., a fluorometer. Such labels can include enzymes and substrates, chromogens, catalysts, fluorescent compounds, phosphorescent compounds, chemiluminescent compounds, and radioactive labels. Typically, a visually detectable label is used, thereby providing for instrumental (e.g. spectrophotometer) readout of the amount of the analyte in the sample. Labels include enzymes such as horseradish peroxidase, galactosidase (alpha and/or beta), and alkaline phosphatase. Suitable substrates include 3,3',5,5'-tetramethylbenzidine (TMB) and 1,2 dioxetane. The method of detection will depend upon the labeled used, and will be apparent to those of skill in the art. Examples of suitable direct labels include radiolabels, fluorophores, chromophores, chelating agents, particles, chemiluminescent agents and the like.

For such embodiments, the label may be a direct label, i.e., a label that itself is detectable or produces a detectable signal, or it may be an indirect label, i.e., a label that is detectable or produces a detectable signal in the presence of another compound. "Labeled second antibody" refers to an antibody that is attached to a detectable label. The label allows the antibody to produce a detectable signal that is related to the presence of analyte in the fluid sample.

Radioactive labels: Suitable radiolabels include, by way of example and not limitation, $^3$H, $^{14}$C, $^{32}$P, $^{35}$S, $^{36}$Cl, $^{57}$Co, $^{131}$I and $^{186}$Re.

"Chromophore" refers to a moiety with absorption characteristics, i.e., are capable of excitation upon irradiation by any of a variety of photonic sources. Chromophores can be fluorescing or non-fluorescing, and includes, among others, dyes, fluorophores, luminescent, chemiluminescent, and electrochemiluminescent molecules.

Examples of suitable indirect labels include enzymes capable of reacting with or interacting with a substrate to produce a detectable signal (such as those used in ELISA and EMIT immunoassays), ligands capable of binding a labeled moiety, and the like. Suitable enzymes useful as indirect labels include, by way of example and not limitation, alkaline phosphatase, horseradish peroxidase, lysozyme, glucose-6-phosphate dehydrogenase, lactate dehydrogenase and urease. The use of these enzymes in ELISA and EMITimmunoassays is described in detail in Engvall, 1980, *Methods Enzym.* 70: 419-439 and U.S. Pat. No. 4,857,453.

"Substrate," "support," "solid support," "solid varrier," or "resin" are interchangeable terms and refer to any solid phase material. Substrate also encompasses terms such as "solid phase," "surface," and/or "membrane." A solid support can be composed of organic polymers such as polystyrene, polyethylene, polypropylene, polyfluoroethylene, polyethyleneoxy, and polyacrylamide, as well as co-polymers and grafts thereof. A solid support can also be inorganic, such as glass, silica, controlled pore glass (CPG), reverse phase silica or metal, such as gold or platinum. "Solid support" includes membranes (e.g. nitrocellulose), microtiter plate (e.g. PVC, polypropylene, polystyrene), dipstick, test tube, and glass or plastic beads. The configuration of a substrate can be in the form of beads, spheres, particles, granules, a gel, a membrane or a surface. Surfaces can be planar, substantially planar, or non-planar. Solid supports can be porous or non-porous, and can have swelling or non-swelling characteristics. A solid support can be configured in the form of a well, depression, or other container, vessel, feature, or location. A plurality of supports can be configured on an array at various locations, addressable for robotic delivery of reagents, or by detection methods and/or instruments. Methods for immobilizing biomolecules are well known in the art, and the antibody can be attached covalently or non-covalently. In one embodiment, the solid support is a stretavidin coated plate to which a biotinylated antibody is non-covalently attached.

In statistics and diagnostic testing, sensitivity and specificity are statistical measures of the performance of a binary classification test. Sensitivity (also called "recall rate") measures the proportion of actual positives which are correctly identified as such (e.g. the percentage of sick people who are correctly identified as having the condition). Specificity measures the proportion of negatives which are correctly identified (e.g. the percentage of healthy people who are correctly identified as not having the condition). These two measures are closely related to the concepts of type I and type II errors. A theoretical, optimal prediction aims to achieve 100% sensitivity (i.e. predict all people from the sick group as sick) and 100% specificity (i.e. not predict anyone from the healthy group as sick), however theoretically any predictor will possess a minimum error bound known as the Bayes error rate.

"Specificity" relates to the ability of the diagnostic test to identify negative results.

$$\text{Specificity} = \frac{\text{\# of True Negatives}}{(\text{\# of True Negatives} + \text{\# of False Positivies})}$$

If a test has high specificity, a positive result from the test means a high probability of the presence of the disease for which the test is testing.

"Sensitivity" relates to the ability of the diagnostic test to identify positive results.

$$\text{Sensitivity} = \frac{\text{\# of True Positives}}{(\text{\# of True Positives} + \text{\# of False Negatives})}$$

If a test has high sensitivity then a negative result would suggest the absence of disease. For example, a sensitivity of 100% means that the test recognizes all actual positives—i.e. all sick people are recognized as being ill. Thus, in contrast to a high specificity test, negative results in a high sensitivity test are used to rule out the disease.

For any test, there is usually a trade-off between the measures. For example: in an airport security setting in which one is testing for potential threats to safety, scanners may be set to trigger on low-risk items like belt buckles and keys (low specificity), in order to reduce the risk of missing objects that do pose a threat to the aircraft and those aboard (high sensitivity). This trade-off can be represented graphically using a receiver operating characteristic (ROC) curve.

In some embodiments, a ROC is used to generate a summary statistic. Some common versions are: the intercept of the ROC curve with the line at 90 degrees to the no-discrimination line (also called Youden's J statistic); the area between the ROC curve and the no-discrimination line; the area under the ROC curve, or "AUC" ("Area Under Curve"), or A' (pronounced "a-prime"); d' (pronounced "d-prime"), the distance between the mean of the distribution of activity in the system under noise-alone conditions and its distribution under signal-alone conditions, divided by their standard deviation, under the assumption that both these distributions are normal with the same standard deviation. Under these assumptions, it can be proved that the shape of the ROC depends only on d'.

The "positive predictive value (PPV)," or "precision rate" of a test is a summary statistic used to describe the proportion of subjects with positive test results who are correctly diagnosed. It is a measure of the performance of a diagnostic method, as it reflects the probability that a positive test reflects the underlying condition being tested for. Its value does however depend on the prevalence of the outcome of interest, which may be unknown for a particular target population. The PPV can be derived using Bayes' theorem.

The PPV is defined as:

$$PPV = \frac{\text{\# of True Positives}}{(\text{\# of True Positives} + \text{\# of False Positives})} = \frac{\text{\# of True Positives}}{\text{\# of Positive calls}}$$

where a "true positive" is the event that the test makes a positive prediction, and the subject has a positive result under the gold standard, and a "false positive" is the event that the test makes a positive prediction, and the subject has a positive result under the gold standard.

"Negative predictive value (NPV)" is defined as the proportion of subjects with a negative test result who are correctly diagnosed. A high NPV means that when the test yields a negative result, it is uncommon that the result should have been positive. In the familiar context of medical testing, a high NPV means that the test only rarely misclassifies a sick person as being healthy. Note that this says nothing about the tendency of the test to mistakenly classify a healthy person as being sick.

The NPV is determined as:

$$NPV = \frac{\text{\# of True Negatives}}{(\text{\# of True Negatives} + \text{\# of False Negatives})} = \frac{\text{\# of True Negatives}}{\text{\# of Negative calls}}$$

where a "true negative" is the event that the test makes a negative prediction, and the subject has a negative result under the gold standard, and a "false negative" is the event that the test makes a negative prediction, and the subject has a positive result under the gold standard.

If the prevalence, sensitivity, and specificity are known, the positive and negative predictive values (PPV and NPV) can be calculated for any prevalence as follows:

$$PPV = \frac{\text{sensitivity} \times \text{prevalence}}{\text{sensitivity} \times \text{prevalence} + (1 - \text{specificity}) \times (1 - \text{prevalence})}$$

$$NPV = \frac{\text{specificity} \times (1 - \text{prevalence})}{(1 - \text{sensitivity}) \times \text{prevalence} + \text{specificity} \times (1 - \text{prevalence})}$$

If the prevalence of the disease is very low, the positive predictive value will not be close to 1 even if both the sensitivity and specificity are high. Thus in screening the general population it is inevitable that many people with positive test results will be false positives.

The rarer the abnormality, the more sure one can be that a negative test indicates no abnormality, and the less sure that a positive result really indicates an abnormality. The prevalence can be interpreted as the probability before the test is carried out that the subject has the disease, known as the prior probability of disease. The positive and negative predictive values are the revised estimates of the same probability for those subjects who are positive and negative on the test, and are known as posterior probabilities. The difference between the prior and posterior probabilities is one way of assessing the usefulness of the test.

For any test result we can compare the probability of getting that result if the patient truly had the condition of interest with the corresponding probability if he or she were healthy. The ratio of these probabilities is called the likelihood ratio, calculated as sensitivity/(1-specificity). (Altman D G, Bland J M (1994). "Diagnostic tests 2: Predictive values", *BMJ* 309 (6947):102).

"Rule-out criteria" "Rule-Out," or "RO" are terms used in a medical differential diagnosis of a disease or condition, in which certain criteria are evaluated in a clinical decision-making process of elimination or inclusion. A subject is "ruled-out" when, upon consideration of the criteria, the subject has been determined not to have met all or a significant number of criteria for having a disease.

II. Devices and Kits Comprising NAG and Methods of Use

In a study conducted in support of the invention, throat swabs were collected from thirty (30) healthy volunteers. Each sample was screened for the presence or absence of Strep A antigen using an immunoassay test strip for detection of Strep A. Unexpectedly, a majority of these swabs gave a positive result, as seen from the data presented in FIG. 1 for each person, denoted by the indicators C-001-C030. The negative control samples are shown as the three bars on the left and indicated "Noswab-Neg", "eswab-Neg" and "eswab-Neb1.5". The positive control sample is on the far right, and denoted "Positive ($2\times10^{-3}$)". At least patients C-001, C-002, C-007, C010, C-013, C-017, C-018, C-020, C-023, C-024 and C-030 were positive for Strep A. It was suspected that a majority of these were false positives because the samples were from healthy individuals. Further investigation was conducted to understand the large number of false positives observed.

Package inserts of several commercial Strep A lateral flow tests, such as QUICK-VUE® Strep A (Quidel Corporation), caution the clinician or person collecting the sample on the swab to avoid touching the swab to tongue, tonsils, cheek or teeth. Such caution was taken in the samples obtained and tested in the study described above, so it was unclear why a large false positive rate was observed. Human biological materials from the tongue, cheek and teeth in a subject's mouth were suspected as a likely cause of false positives using Strep A immunoassays.

Figure 2:
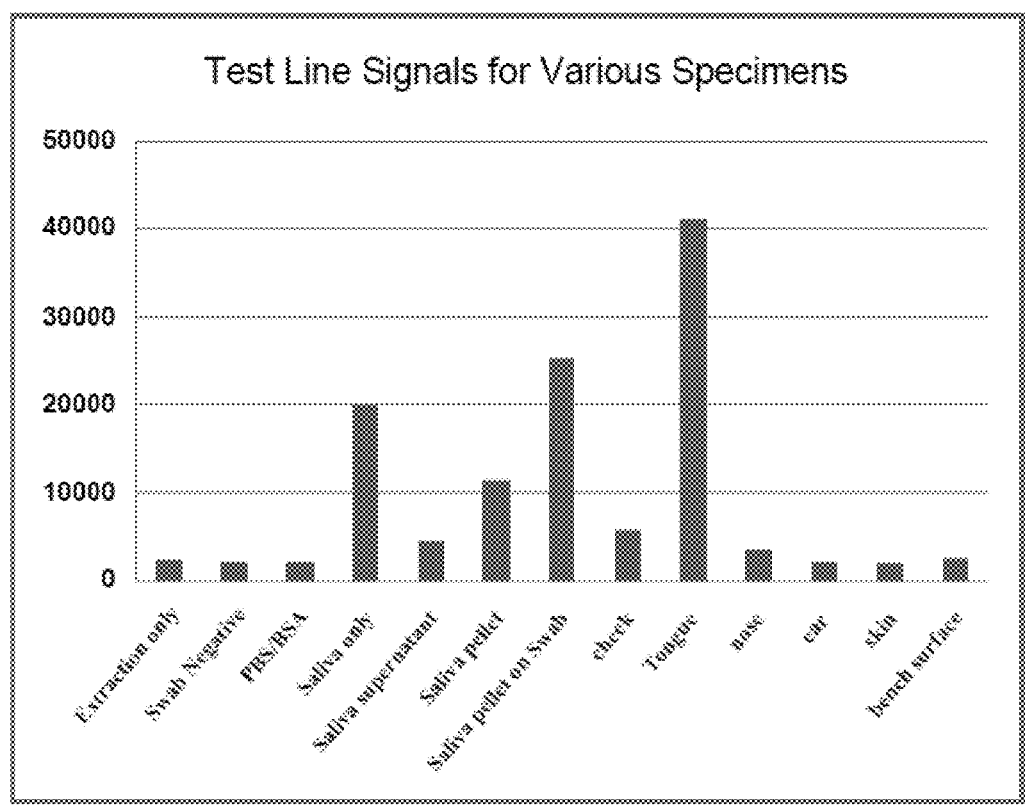

Another study was conducted wherein a swab was used to collect samples from a healthy human of saliva, inner cheek, tongue, nasal passage mucus, ear and skin. As a negative control, a swab of the laboratory bench surface was taken. The swabs were tested for the presence of Strep A using a lateral flow immunoassay. In this study, a sample of saliva was collected and centrifuged to obtain a supernatant and a pellet that were also tested. The results are shown in FIG. 2, and indicate that the samples from the ear, skin and bench surface do not contain Strep A antigen, as these samples have an absolute signal approximately the same as the negative control samples (extraction reagent only, neat swab, PBS/BSA sample). However, the samples obtained from the mouth tissues, saliva, cheek and tongue, were positive for the presence of Strep A, relative to the negative controls.

Figure 3:
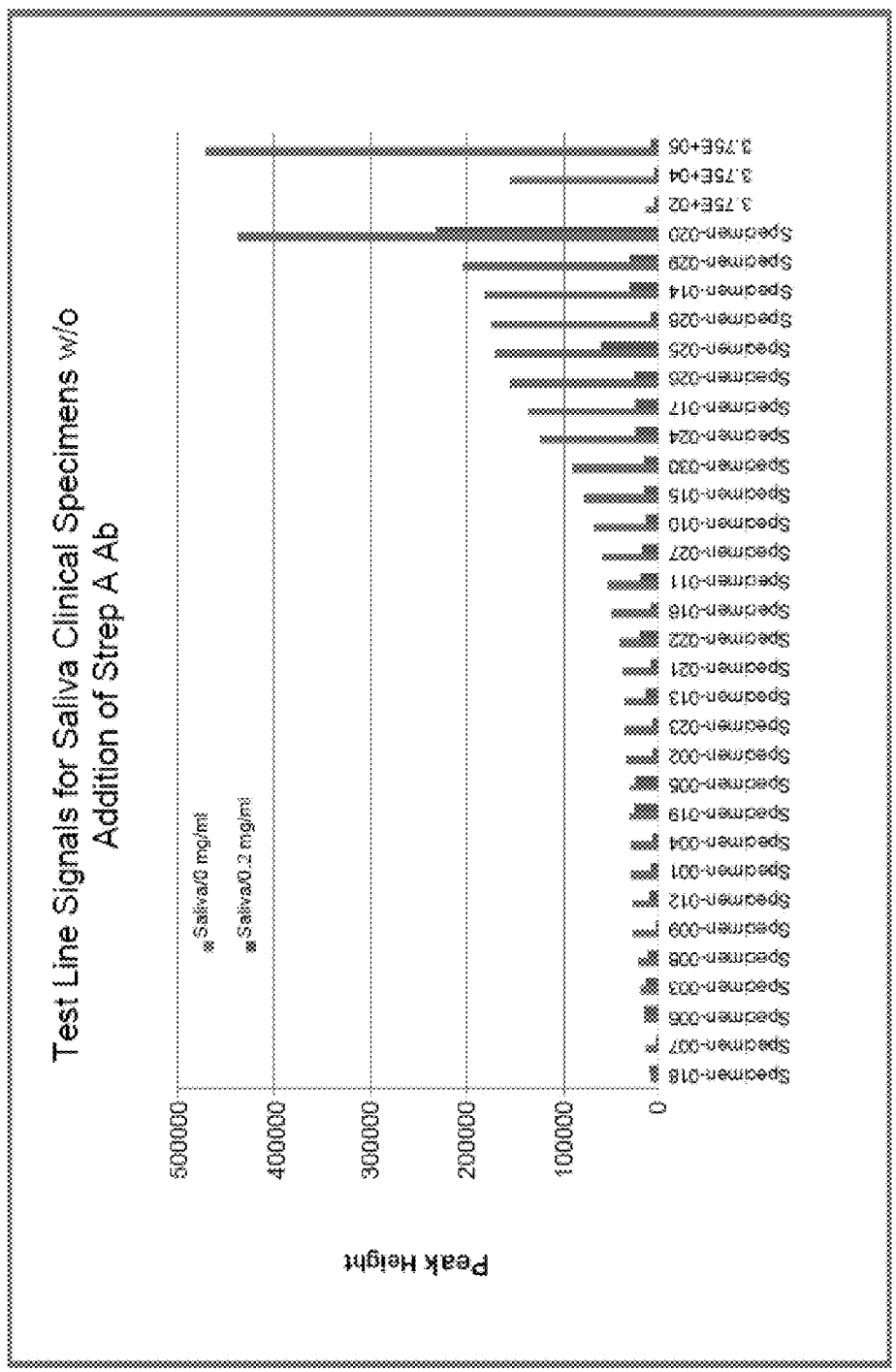

Another study is described in Example 1, wherein saliva samples were tested for the presence or absence of Strep A with and without the addition of a known amount of polyclonal anti-Strep A antibodies to the samples. The results are shown in FIG. 3, where the bar on the left side of each label along the x-axis corresponds to the saliva sample and the bar on the right side of each sample label on the x-axis corresponds to the saliva sample plus addition of anti-Strep A antibodies. The three samples on the far right correspond to quality control standards for Strep A with a known number of organisms with and without addition of anti-strep A antibody. The data in the figure indicates that a component in the saliva samples was causing the false positive readings at the test line in the immunoassay device, rather than the Strep A antigens.

Figure 4:
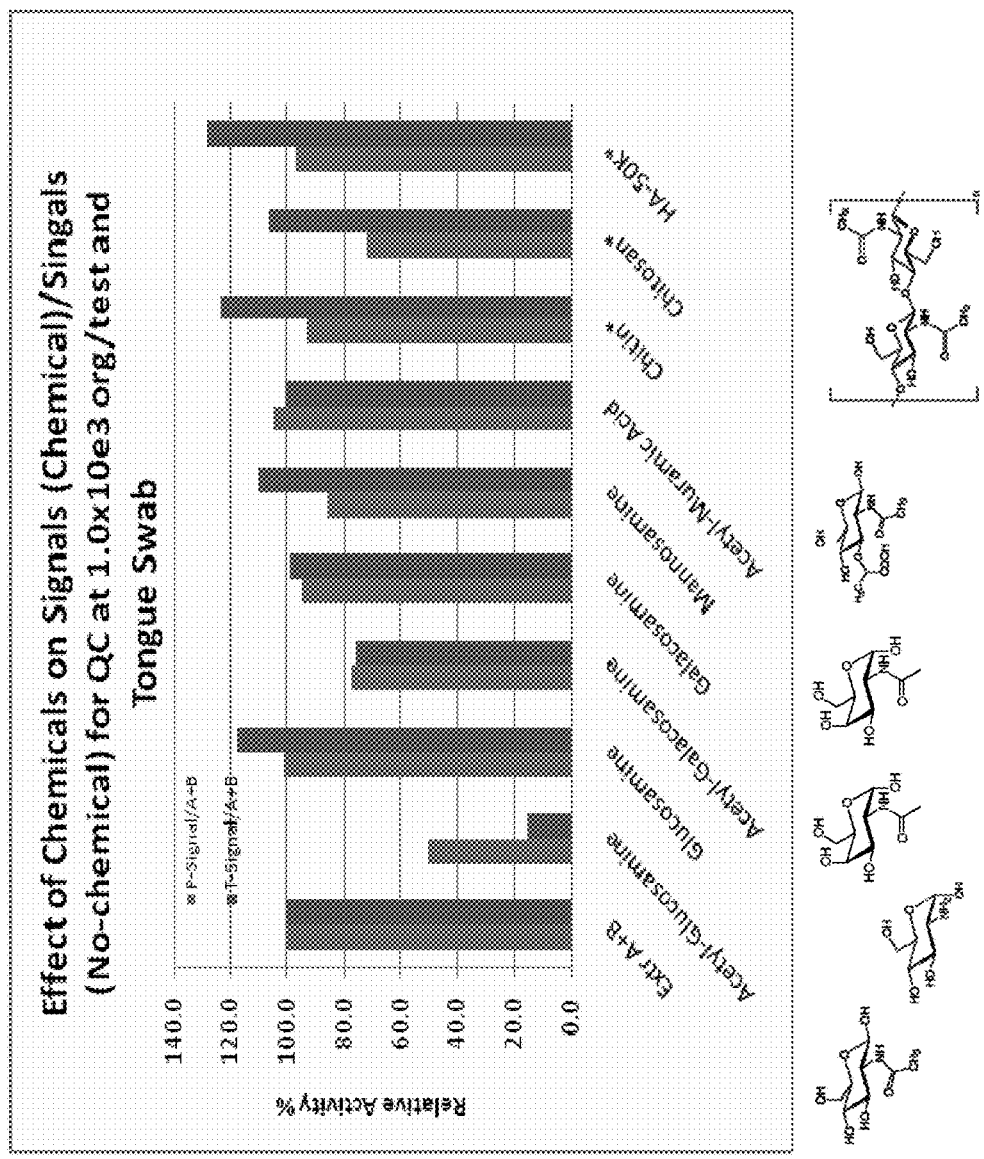

A further study was conducted to identify a possible source or cause of the false positive readings. In the study, detailed in Example 2, a series of chemicals was tested for their ability to inhibit or block the binding of the anti-Strep A polyclonal antibodies in the Strep A immunoassay. The compounds tested included N-acetyl glucosamine (NAG), glucosamine, acetyl-galactosamine, galactosamine, mannosamine, acetyl-muramic acid, chitin, chitosan and hyaluronic acid (HA-50K). Tongue swab samples from a healthy human patient and a Strep A quality control standard ($1\times10^3$ organisms/test) were obtained for testing. Using an immunoassay device for detection of Strep A, the tongue swab sample (right hand bar for each data set in FIG. 4) and the QC standard (left hand bar for each data set in FIG. 4) were each treated with the extraction reagents (such as the extraction reagents in a commercially available QUICK-VUE® Strep A kit) in the presence of the test compound indicated along the x-axis in FIG. 4. As controls and comparators, the Strep A QC standard and a tongue swab sample were each also treated with the extraction reagents (left data set in FIG. 4 labeled "Extr A+B" in FIG. 4; left bar is the positive control QC standard and the right bar of the set of the tongue swab). Results are shown in FIG. 4, where the relative activity of the signal at the test line is shown with respect to its appropriate control. Of the compounds tested, N-acetyl-D-glucosamine (NAG) suppressed the signal resulting from the strep A QC standard at the test line of the immunoassay device by more than 50%, and was able to suppress the signal from the tongue swab to 16% of the control tongue swab signal. The fact that false positive signals from tongue swab specimens were efficiently suppressed by addition of NAG suggests that the Strep A polyclonal antibody contains some non-specific binding activities to human tissue or cells from the tongue/mouth.

Accordingly, in one embodiment, the addition of NAG to an immunoassay is contemplated, where the presence of NAG is effective to reduce non-specific binding between the antibodies in the Strep A polyclonal antibody population and components in the test sample by at least about 50%, more preferably by at least about 60%, 70% or 75% of the signal obtained in the absence of NAG.

Without being bound to theory, the data suggests that the false positive signals from glycoproteins present in epithelial cells inadvertently collected on pharyngeal swab specimens can be efficiently blocked or suppressed by addition of NAG to the immunoassay. The polyclonal anti-Strep A antibodies used in the immunoassay may, in some embodiments, include a population of antibodies that recognize human epithelial cell wall glycoproteins that mimic Group A streptococcal cell wall proteins. By providing a reagent to the immunoassay that can block this population of antibodies, the performance of the immunoassay in terms of overall accuracy by reducing the rate of false positives can be improved. The present invention meets this need by including NAG in the immunoassay device and/or including NAG in extraction reagent(s) provided with the immunoassay.

Immunoassays for detection of Group A *streptococcus* that comprise NAG are contemplated, wherein the assay comprises a lateral flow device that allows for one-step pretreatment and detection of Group A *streptococcus* organisms with enhanced specificity. Immunoassay devices are known in the art, and typically have at least a sample receiving zone, a labeling zone and a capture zone, and can be prepared according to the description in any of U.S. Pat. Nos. 5,415,994; 5,763,262 and 5,770,460, which are incorporated by reference in their entirety.

Accordingly, in one aspect of the disclosure, a device is provided for detecting the presence of Group A *streptococcus* in a sample. Various embodiments of a device are contemplated, and exemplary embodiments are described herein for the purposes of illustration. A skilled artisan will appreciate, however, that the illustrative embodiments are non-limiting to the inventive concepts set forth herein.

Figure 5:
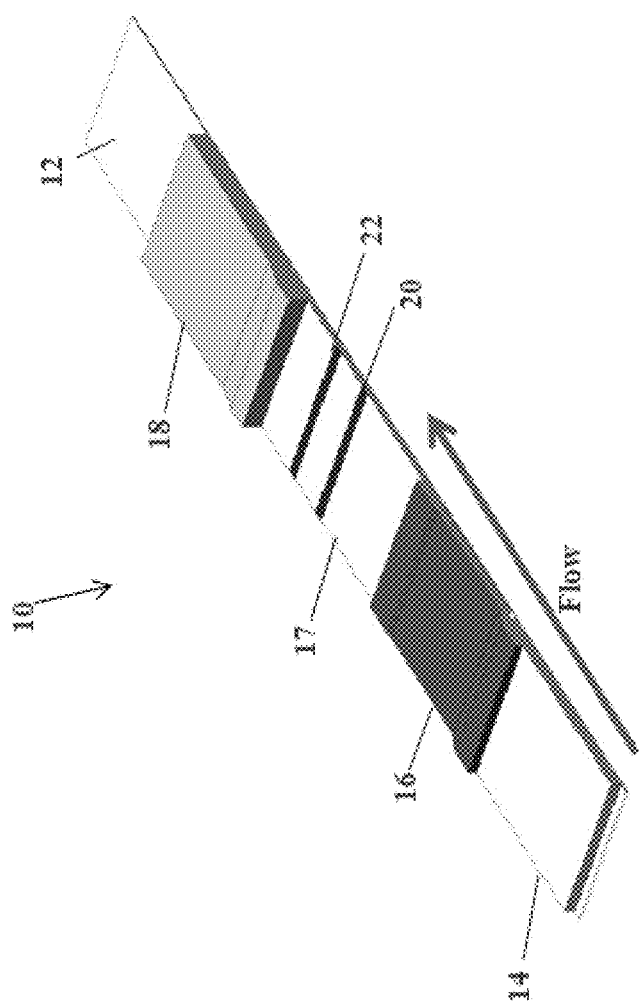

In a general embodiment, a device comprises a series of zones in fluid communication. In a preferred embodiment, a sample receiving zone is in fluid communication with second and subsequent zones, such as a labeling zone, a capture zone, and/or an absorption zone. A first embodiment of a device is depicted in FIG. 5, which shows an immunoassay test strip for detection of Group A *streptococcus*. An exemplary test strip 10 is comprised of a support layer 12 that preferably extends the length of the test strip. Support layer 12 supports in series a sample pad 14, a label pad 16, a nitrocellulose member 17, and an optional absorbent pad 18. On the nitrocellulose member is a test line 20 and a control line 22. For detection of Strep A, the label pad comprises anti-Strep A antibodies, as does the test line. In one embodiment, the antibodies deposited on the label pad comprise a label which aids or permits detection of the antibody. The labeled antibody specifically binds the Strep A antigen as it passes through the label zone. The capture zone comprises a means for specifically binding the labeled antigen thereon. In accord with the present invention, the sample is contacted with N-acetyl-D-glucosamine (NAG) prior to application to the device and/or during its flow through the device. Studies described herein illustrate the improved performance of a device intended for detecting Strep A when NAG is incorporated in the assay. NAG can be incorporated into the device, such as in the sample receiving zone, the labeling zone, or both, and/or the sample can be treated with NAG prior to its application to the sample receiving zone of device.

In one embodiment, the lateral flow immunoassay comprises an immunoassay with label that can be read visually with the unaided eye, such as a colored bead or particle, wherein a collection of such beads or particles at the test line of the immunoassay can be viewed by a user with the naked eye. In another embodiment, the lateral flow immunoassay comprises an immunoassay with a label that is read by an instrument or by an eye with the aid of an instrument. For example, a fluorescent label in the immunoassay is detected using an instrument that can excite the label and the excited label can be read with the instrument, with the eye aided by instrument or with the eye. An exemplary instrument and lateral flow immunoassay is described in U.S. Application No. 61/666,689, which is incorporated by reference herein.

In another aspect, a device is provided for detecting the presence of Group A *streptococcus* in a sample, wherein the device comprises a matrix having (i) a sample receiving zone for receiving a sample containing or suspected of containing a Group A *streptococcus*-specific antigen, (ii) a labeling zone containing an antibody for specifically labeling the antigen as it passes there through and (iii) a capture zone having means for specifically binding the labeled antigen thereon, wherein the sample receiving zone, the labeling zone and the capture zone are arranged on the matrix in a liquid flow path, and wherein the sample receiving zone, the labeling zone, or both contain NAG.

Another embodiment of a device contemplated for use is described in U.S. Pat. No. 5,415,994, which is incorporated by reference herein. In this embodiment, the device comprises a receiving chamber positioned or positionable for fluid contact with a lateral flow immunoassay device, and preferably positioned for fluid communication with a sample receiving zone or a labeling zone of the immunoassay test strip. The biological sample suspect of containing Strep A is received into the receiving chamber, such as by insertion of a swab containing the sample or by dispensing an aliquot of the sample into the receiving chamber. One or more extraction or treatment agents can be additionally added to the receiving chamber or to the swab. In one embodiment, the treatment agent comprises NAG. In one embodiment, the receiving chamber is positioned over the sample receiving zone is dimensioned for receiving a liquid extraction reagent comprising NAG, and, optionally comprises a cylindrical portion for receiving a swab containing a patient sample. The immunoassay test strip comprises a matrix having a sample receiving zone for receiving the extraction liquid containing the treated sample suspected of comprising Strep A antigen, a labeling zone having a polyclonal antibody for specifically labeling the antigen as it passes there through and a capture zone having means for specifically binding the labeled antigen thereon, wherein the sample receiving zone, the labeling zone and the capture zone are arranged on the matrix in a liquid flow path.

In some embodiments of the devices described herein, the extraction reagent provided to treat the biological sample contains NAG. In some embodiments, the labeling zone of the immunoassay device contains NAG. In some embodiments, the capture zone of the immunoassay device contains NAG. In some embodiments, the sample receiving zone of the immunoassay device contains NAG. In some embodiments, all or some of these specified zone comprises NAG, optionally in combination with NAG in an extraction reagent.

Devices as described above were used to further evaluation the effect of NAG on device sensitivity and accuracy. In another study, described in Example 3, different concentrations of NAG in an immunoassay were evaluated for inhibition of Strep A false positive signals. Tongue swabs were taken from a healthy individual, and a Strep A quality control (QC) standard ($2.0 \times 10^3$ organisms/test) were prepared for testing by extracting the sample using the provided extraction reagents, except that NAG was added to the extraction reagents at 0.125 mg/mL, 0.25 mg/mL, 0.5 mg/mL, 1 mg/mL and 2 mg/mL. The samples were deposited on the immunoassay device. Results are shown in FIG. 6 as a function of concentration of NAG present in the extraction reagent for tongue swab samples (diamonds) and for a Strep A quality control standard of $2 \times 10^3$ organisms/test (squares).

Figure 6:
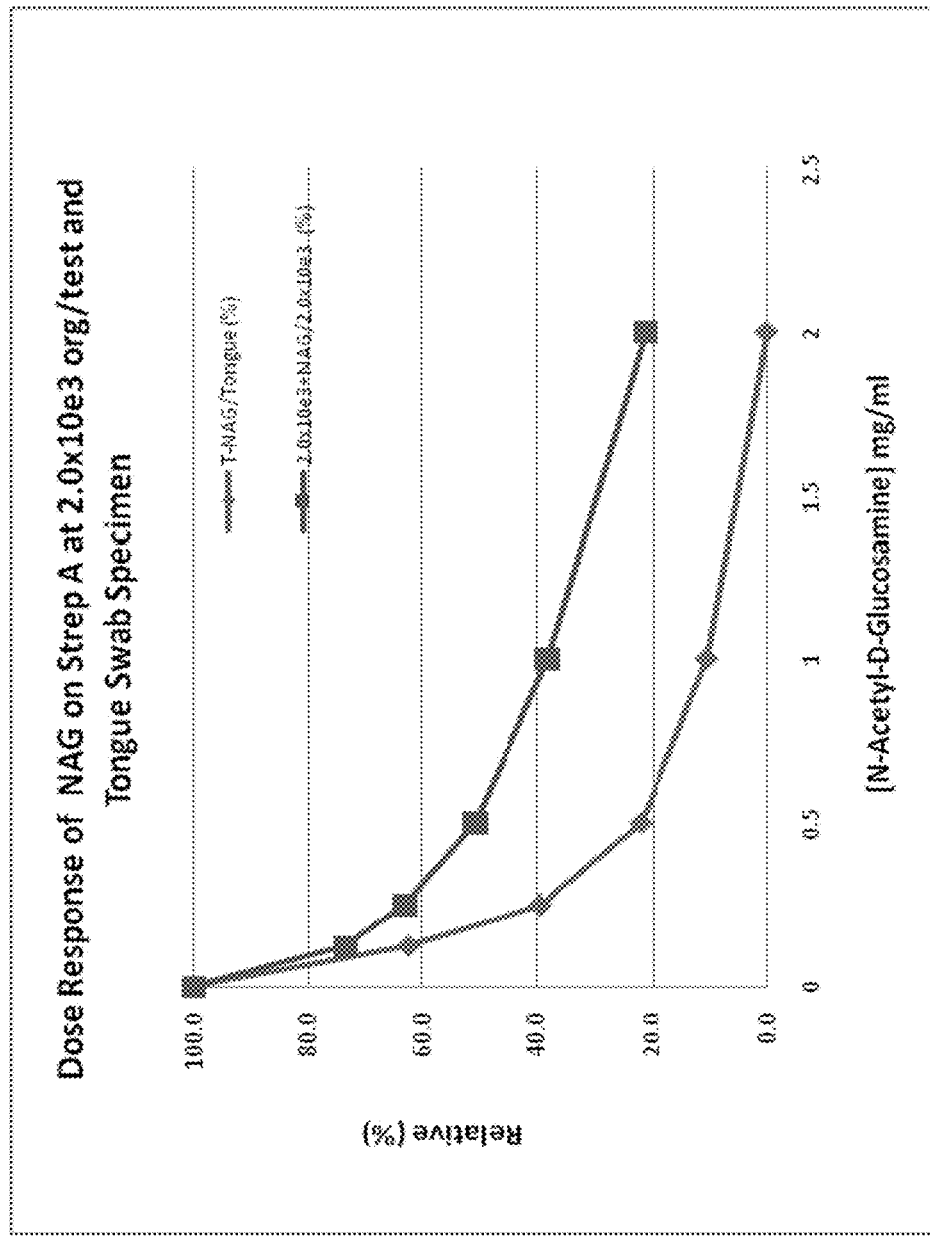

The results in FIG. 6 suggest that NAG more efficiently inhibited the false positives than suppressed Strep A positive signals. NAG present in the immunoassay at a concentration of 0.5 mg/mL (volume of the extraction reagent) was able to inhibit false positives to approximately 20% of the signal observed in the absence of NAG, while at the same NAG concentration the positive signal of Strep A QC standard at $2.0 \times 10^3$ organisms/test remained at 50% of the signal observed in the absence of NAG.

Figure 7:
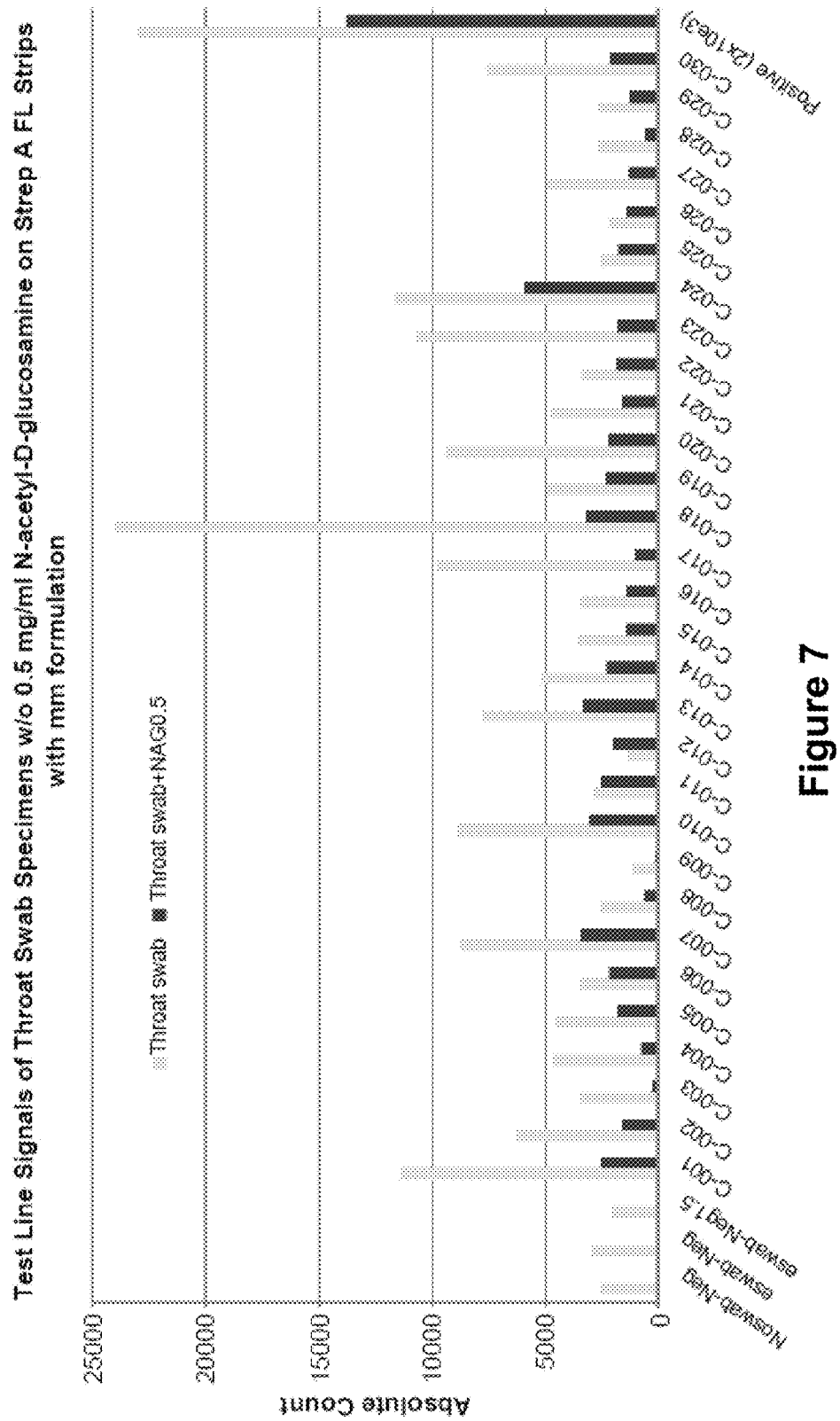

In another study, described in Example 4, the 30 samples originally collected (FIG. 1) were tested again, this time with the addition of 0.5 mg/mL NAG to the extraction reagent provided with the immunoassay test kit. FIG. 7 is a bar graph the presents again the data of FIG. 1 (left bar of each data set) and an aliquot of the saliva sample from the same patient (e.g., C-002) prepared with an extraction reagent comprising 0.5 mg/mL NAG (right hand bar in each of the data sets for each of the indicated patients).

Figure 8:
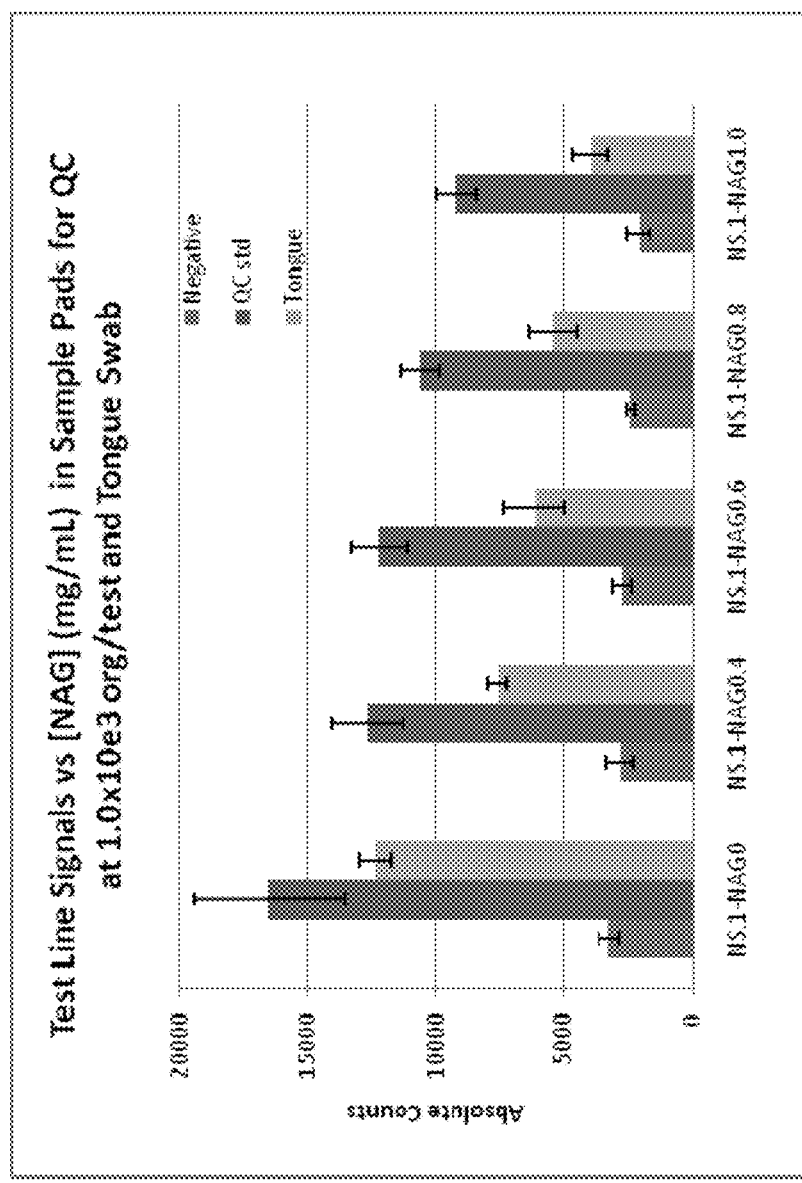

FIG. 8 shows the results of another study where patient samples were tested on an immunoassay device comprising NAG on the sample pad of the device. The devices were prepared by depositing to the sample pad, and allowing to dry, a solution of NAG at concentrations of 0.4 mg/mL, 0.6 mg/mL, 0.8 mg/mL and 1 mg/mL. Tongue swab samples and Strep A QC standards, along with a saline negative control, were each tested on a device. In the bar graph of FIG. 8, the absolute signal at the test line of a Strep A immunoassay device comprising NAG in the sample pad upon application of saline (negative control) is shown in the left bar of each data set, the quality control standard of $2 \times 10^3$ organisms/test is shown in the middle bar of each data set and the tongue swab is shown in the right bar of each data set. Inhibition of the positive signal was observed in the presence of NAG when the Strep A QC standard was tested, as well as for the tongue swab specimens. This result is consistent with the results from study using NAG in the extraction solutions (FIG. 7 and Example 4, above). Accordingly, it is demonstrated that NAG can be included in an appropriate place on the immunoassay device itself or in an off-line extraction medium.

The data presented herein shows that addition of NAG to an immunoassay for Strep A improves the specificity of the test for Group A *streptococcus*, and reduces the rate of false positives. Thus, NAG can be used to effectively reduce false positives in such tests. A skilled artisan will appreciate that the amount of antibody, NAG and sample can be adjusted for optimization of observing a positive signal from *S. pyogenes* while blocking false positives by NAG. The sensitivity and specificity of the tests based on the studies conducted herein are shown in FIG. 9, which shows a calculation of the sensitivity, specificity, positive and negative predictive values of an improved Group A *streptococcus* immunoassay.

Based on the foregoing, and in another aspect, a method is provided for detecting the presence or absence of Strep A in a sample, comprising (a) providing a matrix having (i) a sample receiving zone for receiving a sample containing or suspected of containing a Group A *streptococcus*-specific antigen, (ii) a labeling zone containing an antibody for specifically labeling the antigen as it passes there through and (iii) a capture zone having means for specifically binding the labeled antigen thereon, wherein the sample receiving zone, the labeling zone and the capture zone are arranged on the matrix in a liquid flow path, and (b) contacting the sample receiving zone with the sample, wherein said sample is treated with a liquid reagent comprising NAG prior to contacting; and (c) detecting the presence or absence of the antigen in the capture zone. In one embodiment, the matrix additionally comprises an absorbent zone downstream of the capture zone.

In another aspect, a method is provided to reduce the false positive rate of a lateral flow assay in the detection of Group A *streptococcus* in a liquid sample, wherein, in the lateral flow assay, NAG-binding components of a polyclonal antibody label used in the assay are preferentially bound, the method comprising treating a bibulous matrix with an amount of NAG effective as a blocking agent to enhance the specific binding of the polyclonal antibody to Strep A antigen and reduce the false positive rate of the assay.

In another aspect, a method is provided to reduce the false positive rate of a lateral flow assay in the detection of Group A *streptococcus* in a liquid sample, wherein, in the lateral flow assay, NAG-binding components of a polyclonal antibody label used in the assay are preferentially bound, the method comprising adding to an extraction reagent an amount of NAG effective as a blocking agent to enhance the specific binding of the polyclonal antibody to Strep A antigen and reduce the false positive rate of the assay.

Improvements to a known immunoassay device for detecting Group A *streptococcus* can be made by adding NAG to the sample receiving zone in an amount effective as a blocking agent to enhance the specific binding of at least a portion of the polyclonal antibodies to Strep A antigen, to thereby reduce the false positive rate of the assay. Improvements can also comprise adding NAG to the labeling zone in an amount effective as a blocking agent to enhance the specific binding of the polyclonal antibody to Strep A antigen and reduce the false positive rate of the assay. Improvements can also comprise adding NAG to the extraction reagent in an amount effective as a blocking agent to enhance the specific binding of the polyclonal antibody to Strep A antigen and reduce the false positive rate of the assay.

In some embodiments, the sample is collected through the use of a pharyngeal swab. In some embodiments, the sample is collected through a swab of the pharynx, tongue, cheek, teeth, gums or nasal passages. In some embodiments, a body fluid is sampled, such as urine, saliva, sputum, mucous, blood, blood components such as plasma or serum, amniotic fluid, semen, wound secretions, vaginal secretions, tears, spinal fluid, washings, and other bodily fluids. Included among the sample are swab specimens from, e.g., the cervix, urethra, nostril, and throat.

In some embodiments, the first antibody is a polyclonal antibody that binds to one or more epitopes of Group A *streptococcus*, and also binds to NAG. In some embodiments, the antibody is a population of polyclonal antibodies, the population including a portion of antibodies having specific binding to NAG. In some embodiments, the antibody does not bind to glucosamine, galactosamine, mannosamine, acetyl-muramic acid, chitin, chitosan, and/or hyaluronic acid (e.g., HA-50K).

In some embodiments, the antibody has high specificity and low sensitivity for detecting a Group A *streptococcus* antigen. In some embodiments, the antibody has high sensitivity and low specificity for detecting a Group A *streptococcus* antigen. In some embodiments, the antibody has high specificity and high sensitivity for detecting a Group A *streptococcus* antigen.

Examples of the antibodies used in the immunoassay of the present disclosure may include, but are not limited to a polyclonal antibody, such as an affinity purified rabbit anti-Strep A antibody.

Illustrative publications describing components of precursor compositions, methods and kits, as well as various antibodies for detecting Group A *streptococcus* include the following: U.S. Pat. Nos. 5,415,994; 5,763,262 and 5,770,460. All of these patents, applications and publications are incorporated by reference herein, in their entirety.

Kits

Kits comprising an immunoassay device as described herein are also contemplated. In addition to the immunoassay device, the kits may additionally include any one or more of written instructions for using the device and collecting a biological sample, an instrument or tool for collecting a biological sample, labels for marking the device, a container or vial containing a reagent for preparing a treated sample. The kits may additionally include instructions for reading and interpreting the results of an assay. The kits may further comprise reference samples that may be used to compare test results with the specimen samples. In one embodiment the kits include a swab for collecting a biological sample, and instructions for use of the assay and for collecting the sample, wherein the instructions do not contain a caution against contacting, for example, one or more of the back of the throat, tonsils, cheek or tongue.

Accordingly, in another aspect, a kit is provided, comprising (a) a device comprising a matrix having (i) a sample receiving zone for receiving a sample containing or suspected of containing a Group A *streptococcus*-specific antigen, (ii) a labeling zone containing an antibody for specifically labeling the antigen as it passes therethrough and (iii) a capture zone having means for specifically binding the labeled antigen thereon, and, optionally (iv) an absorbent zone, wherein the sample receiving zone, the labeling zone and the capture zone (and the optional absorbent if present) are arranged on the matrix in a liquid flow path; and (b) a container comprising an extraction reagent; wherein at least one of the extraction reagent, the sample receiving zone and the labeling zone contain NAG.

Example 6 summarizes a study conducted using a kit comprised of a lateral flow immunoassay test strip housed in a cassette with a sample receiving chamber, a vial with a reagent solution and a dropper tip that fit securely on the open end of the vial, a sterile rayon swab, a positive control swab that was coated with heat-inactivated, non-infectious Group A *Streptococcus*, a negative control swab that was coated with heat-inactivated, non-infectious Group C *Streptococcus*, and instructions for use. The test kit was used in a clinical study where two throat swabs were obtained from 533 patients with symptoms suggestive of bacterial pharyngitis.

The lateral flow immunoassay test strip used in the study of Example contained NAG in dried form on the sample pad of the test strip (see FIG. 5). The test strip was designed to work in conjunction with an instrument capable or reading a fluorescent or luminescent signal emitted from the test line and the control line on the test strip. The results of the study are detailed in Example 6, where it can be seen that the sensitivity and specificity were 99% and 96%, respectively.

EXAMPLES

The following examples describe exemplary assays that can be performed using the presently disclosed methods and compositions. However, the present disclosure shall in no way be considered to be limited to the particular embodiments described below.

Example 1: Study Using Saliva Samples from Healthy Volunteers

Saliva specimens were collected from thirty (30) healthy donors. As a positive control a quality control (QC) standard for Strep A consisting of a known number of antigens was obtained. QC standards with $3.75 \times 10^2$ organisms/test, $3.75 \times 10^4$ organisms/test and $3.75 \times 10^5$ organisms/test were obtained. An aliquot of each saliva specimen was deposited on a lateral flow immunoassay test strip comprising similar to that shown in FIG. 5 and comprising polyclonal antibodies specific for Strep A antigen with a fluorescent label. A second aliquot of each saliva specimen was combined with a known quantity (2 mg/mL) of affinity purified polyclonal Strep A antibody. The saliva plus antibody samples were deposited on the immunoassay device, and the test line of the immunoassay device was visually observed for the presence of a fluorescent signal indicative of antigen. The results are shown in FIG. 3.

As seen in FIG. 3, some of the saliva specimens indicated a positive signal at the test line of the immunoassay device, when read using a fluorescent analyzer. Anti-Strep A antibody added to the extraction mix when treating the sample inhibited the positive signal, as seen by the right hand bar for each sample in FIG. 3. Presence of the anti-Strep A antibody in the saliva samples and the QC Standards attenuated the positive signals differently. The attenuation in the presence of Strep A antibody in the saliva specimens was less than on Strep A QC Standards. This can be seen by taking the ratios of the signals in the presence and absence of the antibodies, as shown in Table 1, below. These results indicate that a component in the saliva specimens other than Strep A antigen resulted in false positive signal.

TABLE 1

| | Saliva ID | | | | | | | | | | | | | | | | |
|---|---|---|---|---|---|---|---|---|---|---|---|---|---|---|---|---|---|
| | #1 | #2 | #3 | #4 | #5 | #6 | #7 | #8 | #9 | #10 | #11 | #12 | #13 | #14 | #15 | #16 | #17 |
| Saliva/Saliva + Ab | 3.2 | 4.1 | 1.3 | 4.0 | 1.3 | 1.0 | 3.0 | 1.7 | 5.5 | 4.7 | 2.7 | 2.8 | 2.6 | 5.4 | 5.0 | 5.1 | 5.1 |

| | Saliva ID | | | | | | | | | | | | | | | |
|---|---|---|---|---|---|---|---|---|---|---|---|---|---|---|---|---|
| | #18 | #19 | #20 | #21 | #22 | #23 | #24 | #25 | #26 | #27 | #28 | #29 | #30 | QC Standard $3.75 \times 10^2$ | QC Standard $3.75 \times 10^4$ | QC Standard $3.75 \times 10^5$ | Org/test |
| Saliva/Saliva + Ab | 0.8 | 1.2 | 1.9 | 3.8 | 1.9 | 4.7 | 4.6 | 2.8 | 5.5 | 3.3 | 18.4 | 6.0 | 5.4 | 2.1 | 27.5 | 51.2 | |

Example 2: Analysis of Saccharide Compounds on Observed False Positive Results Compounds composed of or having structures similar to those in bacterial cell wall and human tissues were identified and selected for investigation for ability to inhibit generation of a positive signal on a strep A immunoassay test. The chemicals selected for study were N-acetyl-D-glucosamine (NAG), glucosamine, acetyl-galactosamine, galactosamine, mannosamine, acetyl-muramic acid, chitin, chitosan and hyaluronic acid (HA-50K).

In the study, tongue swab samples from a healthy human patient were obtained. A Strep A quality control standard ($1 \times 10^3$ organisms/test) was also obtained for testing. The tongue swab sample and the QC standard sample were each treated with one of the test compounds and the sample was then deposited on an immunoassay device for detection of Strep A. As controls and comparators, the strep A QC standard and a tongue swab were each treated with the extraction reagents provided with the Strep A immunoassay test kit (left data set in FIG. 4 labeled "Extr A+B" in FIG. 4; left bar is the positive control QC standard and the right bar of the set of the tongue swab). Results are shown in FIG. 4, where the relative activity of the signal at the test line is shown with respect to its appropriate control for the tongue swab sample (right hand bar for each data set in FIG. 4) and the QC standard sample (left hand bar for each data set in FIG. 4). Of the compounds tested, N-acetyl-D-glucosamine (NAG) suppressed the signal resulting from the strep A QC standard at the test line of the immunoassay device by more than 50%, and was able to suppress the signal from the tongue swab to 16% of the control tongue swab signal. The fact that false positive signals from tongue swab specimens can be efficiently suppressed by addition of NAG suggests that the affinity purified Strep A antibody contains some non-specific binding activities to human tissue or cells from the tongue/mouth.

Example 3: Dose Responses of Nag on Positive and False Positive Signals

Six tongue swabs were taken from a healthy individual. A Strep A quality control (QC) standard with $2.0 \times 10^3$ organisms/test was obtained. The swabs and the QC standards were prepared for testing using an immunoassay device for detection of Strep A using polyclonal Strep A antibodies with a fluorescent label. Each sample was admixed with a reagent comprising NAG at 0.125 mg/mL, 0.25 mg/mL, 0.5 mg/mL, 1 mg/mL and 2 mg/mL. The samples were deposited on the immunoassay device, and the test line was visually observed using a fluorescence analyzer for the presence of a positive signal. Results are shown in FIG. 6 as a function of concentration of NAG present in the extraction reagent for tongue swab samples (diamonds) and for a Strep A quality control standard of $2 \times 10^3$ organisms/test (squares).

Example 4: Immunoassay Comprising NAG in Extraction Reagents

Thirty throat swabs collected from healthy donors were tested on an immunoassay for Strep A wherein NAG was added to the extraction mixture at a concentration of 0.5 mg/mL. The extracted samples were deposited on an immunoassay, and the test line was viewed using a fluorescence analyzer to obtain an absolute count of signal emitted. An aliquot of the sample from each patient was also tested without using NAG in the extraction reagent (data in FIG. 1, and represented in FIG. 7 for comparison). Results are shown in FIG. 7, where the bar on the right hand side of each data set for each patient corresponds to the sample prepared in the presence of NAG. The results show that some throat swab specimens from healthy donors can result in a strong false positive signal, but these false positives can be suppressed dramatically by 0.5 mg/mL NAG. See specimen #18 ("C-018"), in particular. Specimen #24 was ("C-024") confirmed to be Strep A positive by cell culture.

Example 5: Immunoassay Comprising NAG in Sample Pad of Immunoassay Device

Immunoassay devices were prepared with a known quantity of NAG in the sample pad. The devices were prepared by depositing to the sample pad, and allowing to dry, a solution of NAG at concentrations of 0.4 mg/mL, 0.6 mg/mL, 0.8 mg/mL and 1 mg/mL.

Tongue swab samples and Strep A QC standards, along with a saline negative control, were each tested on an immunoassay device with each concentration of NAG. Results are shown in FIG. 8, where the absolute signal at the test line of a Strep A immunoassay device comprising NAG in the sample pad upon application of saline (negative control) is shown in the left bar of each data set, the quality control standard of $2 \times 10^3$ organisms/test is shown in the middle bar of each data set and the tongue swab is shown in the right bar of each data set.

Example 6: Specificity and Sensitivity of Strep a Immunoassay Test Strips Comprising NAG in Sample Pad Kits comprising a immunoassay test strip for detection of Strep A were prepared. The kits comprised the immunoassay test strip housed in a cassette with a sample receiving chamber, a vial with a reagent solution and a dropper tip that fits securely on the open end of the vial, a sterile rayon swab, a positive control swab that is coated with heat-inactivated, non-infectious Group A *Streptococcus*, a negative control swab that is coated with heat-inactivated, non-infectious Group C *streptococcus*, and instructions for use. The immunoassay test strip comprised NAG on the sample pad of the test strip and was designed with a fluorescent label readable by an instrument.

The test kits was used in a clinical study where two throat swabs were obtained from 533 patients with symptoms suggestive of bacterial pharyngitis. One throat swab was transported on cold ice packs to a central Reference Laboratory, streaked on a sheep blood agar plate (SBA) and cultured for up to 48 hours. Immediately after streaking, this same swab was tested in the fluorescent immunoassay test strip. The performance of the fluorescent immunoassay test strip was determined by comparison of its result to the corresponding culture result. Bacterial cultures with 10 or more Group A *streptococcus* (GAS)-positive colonies in the first quadrant of the streak plate, and zero or more in the other three quadrants were considered culture-positive. The results from this analysis are presented in Table 6-1. SBA plates showing rare colonies, i.e. less than 10 colonies in the first quadrant and no growth in the other quadrants, were not included.

TABLE 6-1

Fluorescent Immunoassay results and
Culture plate results from same swab

|  | SBA Culture: Positive | SBA Culture: Negative |
|---|---|---|
| Immunoassay test: Positive | 70 | 16 |
| Immunoassay test: Negative | 0 | 432 |
| Total | 70 | 448 |

From this data, the sensitivity is 70/70 (100%) (95% confidence interval (C.I.) 94-100%); specificity is 432/448 (96%) (95% C.I. 94-98%); the positive predictive value is 81% and the negative predictive value is 100%.

The distribution of GAS-positive cultures based on levels of bacterial growth on SBA plates and the corresponding results obtained with the fluorescent immunoassay test strip are presented in Table 6-2. Classification of culture results was also determined. Classification was based on the number of GAS positive colonies in each quadrant of the streaked plate and ranged from rare (less than 10 colonies in the first quadrant and no growth in the other quadrants) to 4+ (greater than 10 colonies in all four quadrants). The fluorescent immunoassay test strip results based on this culture classification are presented in Table 6-2.

TABLE 6-2

Culture Classification of Throat Swab Specimens and Corresponding Sofia Strep A FIA Results

| Culture Classification | Fluorescent Immunoassay Test Strip Result |
|---|---|
| Rare | 10/15 (67%) |
| 1+ | 9/9 (100%) |
| 2+ | 19/19 (100%) |
| 3+ | 25/25 (100%) |
| 4+ | 17/17 (100%) |

The other throat swab, collected from the same patient, was tested directly in the physician's office or clinic without streaking on SBA. The results were compared to culture obtained with the other swab (see Table 6-1 above). The sensitivity and specificity obtained with direct testing of this swab were 99% (69/70) and 96% (426/442), respectively. There were 15 rares (see Table 6-2 above) and six invalids; these were excluded from the calculations of clinical accuracy. The fluorescent immunoassay test strip was also used to confirm the identification of presumptive Group A *streptococcus* colonies on sheep blood agar plates. For culture confirmation, the test was 100% sensitive and 95% specific (Table 6-3).

TABLE 6-3

Confirmation of Bacterial Culture Results with Sofia Strep A FIA

|  | SBA Culture: Positive | SBA Culture: Negative |
|---|---|---|
| Immunoassay test: Positive | 17 | 1 |
| Immunoassay test: Negative | 0 | 20 |
| Total | 17 | 21 |

From this data, the sensitivity is 17/17 (100%) (95% C.I. 78-100%\); specificity is 20/21 (96%) (95% C.I. 76-100%)); the positive predictive value is 94% and the negative predictive value is 100%.

While various specific embodiments have been illustrated and described, skilled artisans will recognize various modifications, permutations, additions and sub-combinations thereof, and will appreciate that these can be made without departing from the spirit and scope of the present disclosure. Therefore, it is to be understood that the disclosure is not to be limited to the specific embodiments disclosed herein, as such are presented by way of example. Although specific terms are employed herein, they are used in a generic and descriptive sense only and not for purposes of limitation.

All literature and similar materials cited in this application, including, but not limited to, patents, patent applications, articles, books, treatises, internet web pages and other publications cited in the present disclosure, regardless of the format of such literature and similar materials, are expressly incorporated by reference in their entirety for any purpose to the same extent as if each were individually indicated to be incorporated by reference. In the event that one or more of the incorporated literature and similar materials differs from or contradicts the present disclosure, including, but not limited to defined terms, term usage, described techniques, or the like, the present disclosure controls.

What is claimed is:

1. A device, comprising: a matrix comprising (i) a sample receiving zone, (ii) a labeling zone containing a labeled antibody with specific binding to Group A *streptococcus* antigen, to form a labeled antibody-bound antigen, and (iii) a capture zone having means for specifically binding the antibody-bound antigen thereon, wherein the sample receiving zone, the labeling zone and the capture zone are arranged on the matrix in a liquid flow path, and wherein at least one of the sample receiving zone and the labeling zone comprises N-acetyl-D-glucosamine (NAG) monomer which reduces the rate of false positives for providing accurate detection of Group A *streptococcus* infection.

2. The device of claim 1, wherein the antibody is a polyclonal antibody.

3. The device of claim 2, wherein the antibody is fluorescently labeled.

4. The device of claim 1, wherein the means for specifically binding the antigen-bound antibody is a capture antibody.

5. The device of claim 4, wherein the capture antibody is a polyclonal antibody.

6. A method for detecting the presence or absence of Group A *streptococcus* in a biological sample, comprising:
providing a device according to claim 1;
placing a biological sample on the device; and
determining the presence or absence of Group A *streptococcus*.

7. The method of claim 6, further comprising:
providing an instrument for collecting the biological sample; and
collecting a biological sample on the instrument.

8. The method of claim 6, further comprising:
providing instructions for use, wherein the instructions do not caution to not touch the tongue, sides or top of mouth with the instrument when collecting the sample.

* * * * *

UNITED STATES PATENT AND TRADEMARK OFFICE
CERTIFICATE OF CORRECTION

PATENT NO. : 10,168,329 B2
APPLICATION NO. : 13/563542
DATED : January 1, 2019
INVENTOR(S) : Ren et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 662 days.

Signed and Sealed this
Twenty-fourth Day of December, 2019

Andrei Iancu
*Director of the United States Patent and Trademark Office*